(12) United States Patent
Cabak et al.

(10) Patent No.: US 6,582,443 B2
(45) Date of Patent: Jun. 24, 2003

(54) APPARATUS AND METHODS FOR ENHANCING THE FUNCTIONAL LONGEVITY AND FOR FACILITATING THE IMPLANTATION OF MEDICAL DEVICES

(75) Inventors: James E. Cabak, Plymouth, MN (US); Steven T. Deininger, Savage, MN (US); John W. Westrum, Jr., Prior Lake, MN (US)

(73) Assignee: AMS Research Corporation, Minnetonka, MN (US)

( * ) Notice: Subject to any disclaimer, the term of this patent is extended or adjusted under 35 U.S.C. 154(b) by 58 days.

(21) Appl. No.: 09/749,301

(22) Filed: Dec. 27, 2000

(65) Prior Publication Data

US 2002/0082619 A1 Jun. 27, 2002

(51) Int. Cl.$^7$ .............................................. A61B 17/08
(52) U.S. Cl. ....................................... 606/151; 606/148
(58) Field of Search ................................. 606/151, 148

(56) References Cited

U.S. PATENT DOCUMENTS

| | | |
|---|---|---|
| 3,054,406 A | 9/1962 | Usher |
| 3,124,136 A | 3/1964 | Usher |
| 3,384,073 A | 5/1968 | Walton |
| 3,789,828 A | 2/1974 | Schulte |
| 4,857,041 A | 8/1989 | Annis et al. |
| 4,938,760 A | 7/1990 | Burton et al. |

(List continued on next page.)

FOREIGN PATENT DOCUMENTS

| WO | WO 93/17635 | 9/1993 |
|---|---|---|
| WO | WO 00/74633 | 12/2000 |
| WO | WO 01/39670 | 6/2001 |

OTHER PUBLICATIONS

Pelosi II, Marco A. et al., The Yama UroPatch™ Sling for Treatment of Female Stress Urinary Incontinence: A Pilot Study, Journal of Laparoendoscopic & Advanced Surgical Techniques, vol. 12, No. 1, (2002), pp 1–11.
Pelosi II, Marco A., Yama UroPatch™ Surgical Technique for Transvaginal Urethral Sling Procedure: Optimizing Clinical Outcomes, Source: Yama, Inc., pp 1–11.
Choe, John M. et al. Autologous, Cadaveric, and Synthetic Materials Used in Sling Surgery: Comparative Biomechanical Analysis, Elsevier Science, Inc., Basic Science, (2001), pp 482–486.
Chaikin, Davidk C. et al., Weakened Cadaveric Fascial Sling: An Unexpected Cause of Failure, The Journal of Urology, vol. 160, 2151 (Dec. 1998) p. 2151.

*Primary Examiner*—Peter Nerbun
*Assistant Examiner*—Katherine M Moran
(74) *Attorney, Agent, or Firm*—Jeffrey J. Hohenshell

(57) ABSTRACT

Surgical apparatus and associated methods of use are provided for enhancing the functional life-span of medical implants and for facilitating their implantation, particularly for medical devices designed to support anatomical structures. The apparatus comprises a reinforcing fastener guide for fixedly mounting or interlocking onto the surface of a medical device such as a urethral sling or the like. Formed of surgical grade metals or plastics, the attached reinforcing fastener guide defines an easily identified location for the implanting surgeon to position one or more surgical fasteners, such as a suture, to the patient's body in order to permanently position the medical implant. This greatly simplifies and shortens the implantation protocol while substantially reducing undesirable mechanical stresses within the implant at these attachment points, thereby increasing the useful life of the implanted medical device.

19 Claims, 5 Drawing Sheets

U.S. PATENT DOCUMENTS

| | | |
|---|---|---|
| 4,969,892 A | 11/1990 | Burton et al. |
| 5,222,988 A | 6/1993 | Riley |
| 5,337,736 A | 8/1994 | Reddy |
| 5,362,294 A | 11/1994 | Seitzinger |
| 5,383,904 A | 1/1995 | Totakura et al. |
| 5,474,518 A | 12/1995 | Farrer Velazquez |
| 5,611,515 A | 3/1997 | Benderev et al. |
| 5,669,935 A | 9/1997 | Rosenman et al. |
| 5,934,283 A | 8/1999 | Willem et al. |
| 5,997,554 A * | 12/1999 | Thompson .................. 606/148 |
| 6,010,447 A | 1/2000 | Kardjian |
| 6,039,686 A | 3/2000 | Kovac |
| 6,042,534 A | 3/2000 | Gellman et al. |
| 6,042,536 A * | 3/2000 | Tihon et al. .................. 600/37 |
| 6,050,937 A | 4/2000 | Benderev |
| 6,110,101 A | 8/2000 | Tihon et al. |
| 6,117,067 A | 9/2000 | Gil-Vernet |
| 6,245,082 B1 * | 6/2001 | Gellman et al. ............. 606/151 |
| 6,500,194 B2 | 12/2002 | Benderev et al. |
| 2001/0000533 A1 | 4/2001 | Kovac |
| 2002/0091373 A1 | 7/2002 | Berger |
| 2002/0147382 A1 | 10/2002 | Neisz et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0156489 A1 | 10/2002 | Gellman et al. |

* cited by examiner

APPARATUS AND METHODS FOR ENHANCING THE FUNCTIONAL LONGEVITY AND FOR FACILITATING THE IMPLANTATION OF MEDICAL DEVICES

BACKGROUND OF THE INVENTION

The present invention is generally directed to apparatus and methods for increasing the functional longevity and useful life of implantable medical devices while facilitating, shortening, and simplifying their implantation protocols. More particularly, the present invention is directed to apparatus and to associated methods for reducing mechanical stresses exerted on such medical devices by sutures and other surgical attachment mechanisms, both during and after implantation of the devices. Further, the present invention provides the implanting surgeon with easy to identify and use surgical attachment points which facilitate the implantation procedure relative to conventional devices and methods.

The surgical implantation of medical devices has long been known in the art. Presently, a number of surgical procedures utilize various implantable medical support devices and structures to stabilize organs and other anatomical structures at or near their original natural positions. As a result, these implanted medical devices and the associated surgical implantation procedures used to position them not only prevent or reduce anatomical deterioration of the supported organs and anatomical structures, but provide the added potential benefits of improving the function and, possibly, the functional life of the supported body part.

Such implantable medical support devices have been developed in a wide variety of structural and design configurations, depending upon intended need at the implantation site. For example, simple mesh slings or sheets of material have been used to reinforce abdominal walls following the protrusion of portions of the intestine. These mesh sheets have been formed of a variety of materials ranging from simple, biologically tolerable synthetic cloths to metals that are sutured into position. Alternatively, more exotic structures have been sutured between bones, for example, of the pelvis, to form supporting slings for abdominal organs and structures.

A specific example of one such commonly used medical implant is the urethral sling utilized for treating cases of recurrent urinary incontinence in females. Female recurrent urinary incontinence commonly develops from the loss or weakening of pelvic support of the urethra and/or bladder. Surgical corrective procedures have been developed for this condition which generally utilize a sling to add to the pelvic support of the abdominal organs, including the bladder or bladder neck in their natural positions.

Even though it is possible that the use of subsequent therapeutic protocols in combination with the patient's natural healing process and the added support provided by the implanted sling may improve the naturally existing muscle support of the patient's abdomen, medical implants such as these are intended to remain in stable condition in situ for extended periods of time, measured in years and even in decades. Therefore, it is important that slings and other implantable medical devices be designed with long term, stable functionality in mind.

One way to achieve this stability is to form the sling itself from biologically compatible materials in designs that will be compatible with normal physiological healing processes and that will retain their functional characteristics throughout years of use. Additionally, stable placement of the medical support devices during the implantation procedures also impacts this long-term functionality. For example, a urethral sling may be positioned across the appropriate portion of the abdominal floor to support the bladder or bladder neck by suturing opposing ends of the sling into position suspended from the pelvic structures, e.g., pelvic ischia, the lower most bones depending from each side of the pelvis. This positioning provides added stability beyond that available by simply suturing the sling to tissue structures and connective tissue.

Overall, medical implantation support techniques such as the above have enjoyed widespread success. However, there is always room for improvement. Under the present circumstances, it is known in the art that implanted medical devices such as these undergo physical changes over time as a result of the body's natural healing and immune processes as well as the mechanical stresses imparted into and absorbed by the implants through repeated movement and use. Fabric weaves can shift and fibers can stretch, both contributing to decreases in the amount of support provided by the implant. Similarly, suturing holes in the implant materials may distort and stretch over time under the constant, concentrated forces focused into the sling materials by the direct contact of the fastening sutures cutting into the implants. This stretching and weakening may ultimately result in the inability of the implants to effectively perform their intended tasks, including that of support.

It is worth noting that fastening the implants into position with sutures remains as a very poplar technology. Though somewhat time-consuming during the implantation process, suturing provides the implanting surgeon with the degree of flexibility necessary to produce the best possible results with the implanted medical device. Still, the act of positioning the various sutures utilized in connection with conventional implantation techniques is rather time-consuming. In each case the surgeon must determine a suturing position within the implant material itself and then pass the suturing thread therethrough prior to attaching to pelvic structures, e.g., bony structure or stitching the sutures to softer tissue structures.

Accordingly, a need remains in the art for technologies and designs that can reduce the damage and stretching worn into implanted medical devices by sutures and surgical fastening devices, thereby increasing their functional longevity. A related need exists for technologies and designs that can simplify and facilitate the implantation of these devices.

SUMMARY OF THE INVENTION

These and other objects are achieved by the various apparatus and associated methods of the present invention.

In a broad aspect, the present invention provides novel apparatus that can be added or affixed to existing medical implants or incorporated into their original designs which will increase their functional longevity by distributing normal suture and medical fastener stresses throughout larger structural areas of the medical implants, reducing knifing and subsequent distortion. Utilization of these same devices also facilitates implantation of the medical implants by providing the implanting surgeon with readily identifiable guides, which both tactilely and visually direct the surgeon to the surgical fastener locations that are themselves easy to manipulate and employ during the surgical implantation procedure.

More specifically, the present invention provides readily adaptable apparatus for enhancing the functional longevity and for facilitating the implantation of medical devices through the provision of one or more reinforcing fastener guides fixed upon incorporated into the outer surfaces of the medical devices. Much like a curb or resistive barrier, the reinforcing fastener guides of the present invention provide a stable anchor to the medical implants themselves for the attaching sutures or other surgical attaching fasteners utilized to position the implants. In this manner, the reinforcing fastener guides provide a structural enhancement affixed to the medical implant that distributes compresses and tensile loads imparted into the implant by the surgical fasteners.

Moreover, at the same time, the reinforcing fastener guides of the present invention can be formed in a wide variety of shapes ranging from simple bars, arcs, and crescents to complete circles and polygons defining generally centrally located surgical fastener apertures within each. These novel reinforcing guides not only clearly define a readily discernible suture or fastening location within the implants, but also provide the implanting surgeon with both a visual and tactile indicator for quickly locating and employing the available fastening sites to fix the medical implants in position.

The reinforcing fastener guide apparatus of the present invention can be manufactured and formed from virtually any currently available or anticipated surgical implant materials. For example, biologically compatible materials suitable for the manufacture of implants include surgical grade stainless steel and titanium, ceramics, composites and fiber-reinforced materials, polymers, and bioresorbable materials. Accordingly, the apparatus of the present invention can be formed of any material that is suitable for use in connection with the desired implant. Further, this flexibility of manufacturing materials makes it possible to incorporate the reinforcing fastener guide apparatus of the present invention directly into the medical implants themselves during manufacture. Doing so eliminates another potential step in the implantation process by removing the need to attach or fix the reinforcing fastener guide apparatus to the implants prior to implantation itself.

Either way, if it is determined to be desirable to attach the apparatus of the present invention to an implant, one embodiment of the present invention includes fixation-interlocking mechanisms as part of the apparatus. An exemplary embodiment of the fixation interlocking mechanisms is a projecting pin with an enlarged head, which will penetrate or pierce the surface of the implant and lockingly engage thereto. Additional embodiments enhance this function by providing a complementary backing plate to the apparatus that will receive and lockingly engage the interlocking mechanisms.

An alternative embodiment of the present invention hinges the fastener reinforcing guide to the complementary backing plate so that it is possible to attach the apparatus of the present invention to an implant by positioning an edge of a planar surface of the implant between the hinged components of this embodiment of the present invention and simply snapping or latching the interlocking components shut. Doing so results in positioning the interlocking pins of the apparatus through the implant material into fixed engagement with the complementary backing plate, in a single motion.

In an additional embodiment of the present invention, the reinforcing fastener guide apparatus is also provided with at least one external ring. This ring can be fixed or rotatable about a pivoting attachment to the reinforcing fastener guide. It can function as a suture or surgical fastening aperture, which may be provided in the reinforcing fastener guide itself Alternatively, it can function to add additional fastener apertures to the one or more apertures previously provided in the body of the reinforcing fastener guide itself.

The present invention also provides associated implantation methods that utilize the novel features of the reinforcing fastener guides to simplify and facilitate the implantation of such medical devices. In a broad aspect these methods comprise the steps of fixedly mounting or attaching one or more reinforcing fastener guides of the present invention to one or more portions of the medical device to be implanted, prior to implantation of the device. It should be noted by those skilled in the art that this mounting step can be accomplished by the surgeon as part of the implantation procedure itself or, in the alternative, by the manufacturer of the medical implant, well in advance of the implantation procedure. The next step involves positioning the medical device within a patient's body at the desired implantation site. Finally, at least one surgical fastener, such as a suture, is placed through each of the various reinforcing fastener guides present on the implant in order to secure the various attachment portions of the implant in place within the patient's body.

In this manner, the implanting surgeon is able to rapidly position and secure the medical implant in-place utilizing the unique, clearly identifiable and easily locatable fastener apertures provided by each of the fixedly mounted reinforcing fastener guides of the present invention. Doing so not only shortens and facilitates the implantation procedure, but adds to the potential functional longevity of the implant itself by providing enhanced fixation locations that more evenly distribute tensile loads within the implant; thereby reducing wear and potential weakening of the implant over time.

For example, an exemplary urethral sling of the present invention can be provided with a plurality of reinforcing fastener guides fixedly mounted at opposing corners of the generally rectangular sling material support. Following a conventional surgical access procedure to the target implantation site, the surgeon simply positions the implant so that it can be secured into its proper location. However, unlike the prior art designs which require puncturing the sling material with a surgical fastener or, at a minimum, locating one of several provided suturing holes, the apparatus and methods of the present invention enable the surgeon to simply locate the reinforcing fastener guides and then placing an appropriate suture or other surgical fastening device such as a polymer or metal stud through the readily identifiable aperture in the reinforcing fastener guide to secure that portion of the implant in-place. This procedure is repeated for the each of the remaining reinforcing fastener guides until the implant is securely fastened in-place. The implantation procedure is then completed utilizing a conventional closure process.

A more detailed understanding of these features, and of additional features, objects, and advantages of the present invention will be provided to those skilled in the art from a consideration of the following Detailed Description of the Invention, taken in conjunction with the accompanying Drawings, which will now first be described briefly.

BRIEF DESCRIPTION OF THE DRAWINGS

FIG. 4 is a perspective view of an additional alternative embodiment of the present invention illustrating additional features there of.

DETAILED DESCRIPTION OF THE DRAWINGS

Referring more particularly to the Drawings, the present invention is directed to increasing the functional longevity of implantable medical devices and to facilitating their implantation. This is accomplished in accordance with the teachings of the present invention by providing such known medical implants, as well as future medical implant designs, with at least one reinforcing fastener guide for securing or fixating the implants in position, as appropriate to the design and functional needs of the devices.

In this manner the present invention enhances the functional longevity of the implants by protecting the structural integrity of the implantable medical devices against potentially damaging forces that may be exerted over time on such devices by sutures and other surgical attachment mechanisms following implantation of the devices into a patient. Similarly, the implanted devices are further protected from potentially damaging forces resulting from subsequent movement by that patient which may impart additional stretching or tensile loads into the surgically fixated medical implants.

Additionally, the reinforcing fastener guides and the medical implants of the present invention incorporating these apparatus virtually eliminate the possibility of inadvertent damage to the implants during the surgical implantation procedure by providing the implanting surgeons with easy to locate and use, pre-positioned surgical fastener apertures. Eliminating such inadvertent damage further enhances the functional longevity of the implant while greatly facilitating the surgical implantation of the medical devices as well.

Figure 1:
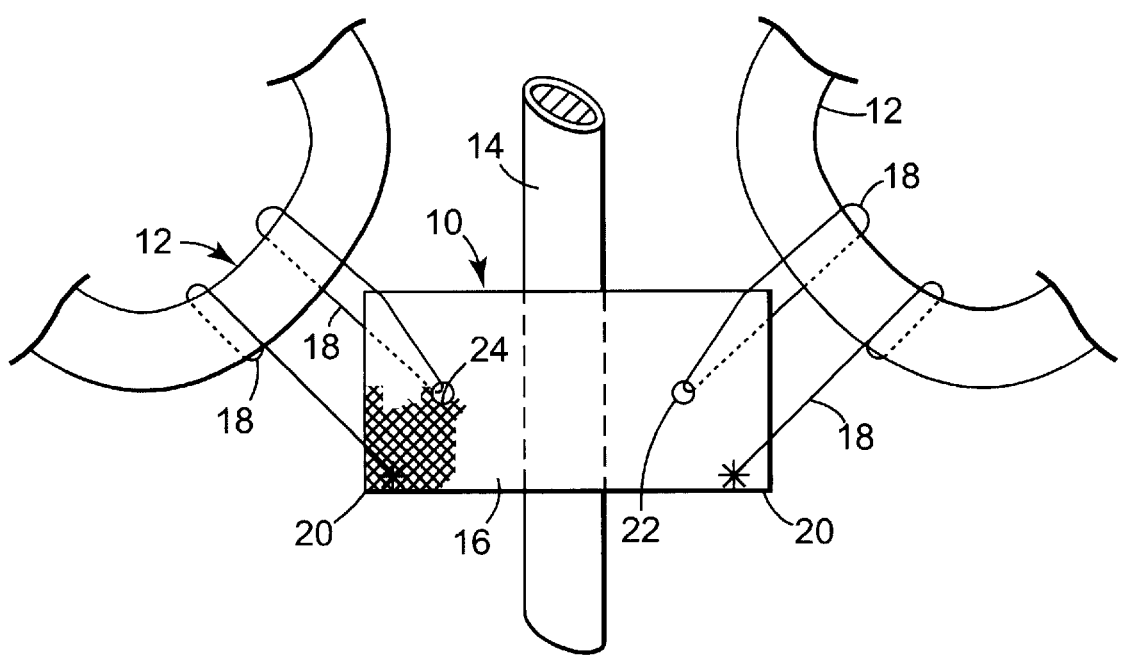
FIG. 1 is a plan view of an exemplary prior art urethral sling illustrating conventional suturing techniques.

Turning now to the Drawings, FIG. 1 illustrates a conventional prior art implantable medical device, in this case, a urethral sling, generally indicated by reference numeral 10. Urethral sling 10 is designed to be sutured in-place, suspended between the opposing pelvic ischia 12, in order to provide added or necessary support to portions of the urethra or bladder neck 14. Prior art urethral sling 10 may be surgically implanted into a patient using any of a variety of known surgical procedures. One such exemplary prior art surgical implantation procedure is discussed in U.S. Pat. No. 6,039,686 to Kovac, the entire disclosure of which is herein incorporated by reference.

As illustrated in FIG. 1, the prior art urethral sling 10 primarily comprises a generally rectangular support 16 suspended between the opposing support structures in the pelvis, e.g., pelvic ischia 12 by sutures 18 to provide added support to bladder neck 14. Sutures 18 are threaded through support 16 in several different ways. The simplest way to thread suture 18 through support 16 is to pierce support 16 with a suturing needle as indicated by pierced hole 20. Alternatively, as known in the art, support 16 may be provided with pre-punched hole 22 through which suture 18 may be passed without puncturing the material forming support 16. An additional prior art feature intended to retain a suture 18 within support 16 is hemmed hole 24. Hemmed hole 24 encircles the pre-punched hole 22 with a sewn seam in an effort to prevent fraying and unraveling of the hole.

Though widely successful in the art, such prior art designs continue to share a weakness imparted by the fact that, under the influence of gravity or physical motion by the implant patient, sutures 18 focus tensile stresses into relatively small, discrete portions of support 16. Over time, these stresses can result in undesirable wear and distortion of the suturing holes in support 16 such that the intended suspending support provided by support 16 may be decreased by naturally occurring slack as the original configuration of the sutures 18 and suture holes changes. In addition, undesirable deformation of the support 16 can occur due to the single point connection of the suture 18 to the edge of the support 16. That is, when the support 16 is placed in tension, the stress induced on the sutures is localized at the single hole 22 at each edge of the support 16.

Figure 2:
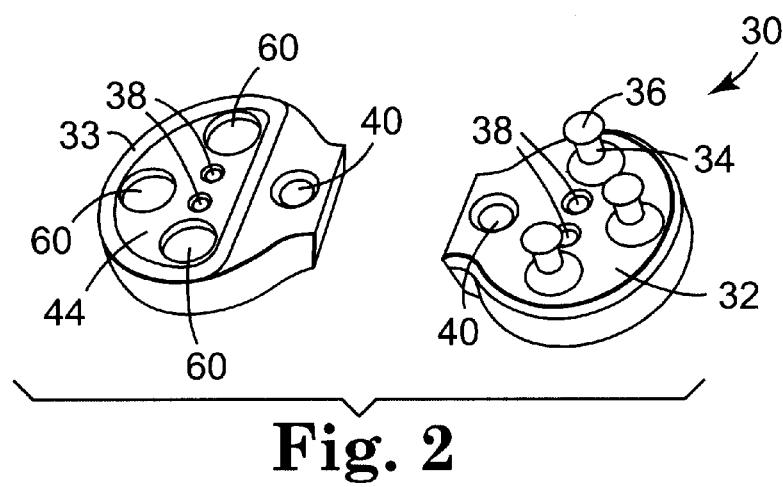
FIG. 2 is a perspective view of an exemplary reinforcing fastener guide of the present invention illustrating various structural and functional aspects thereof.
Figure 6:
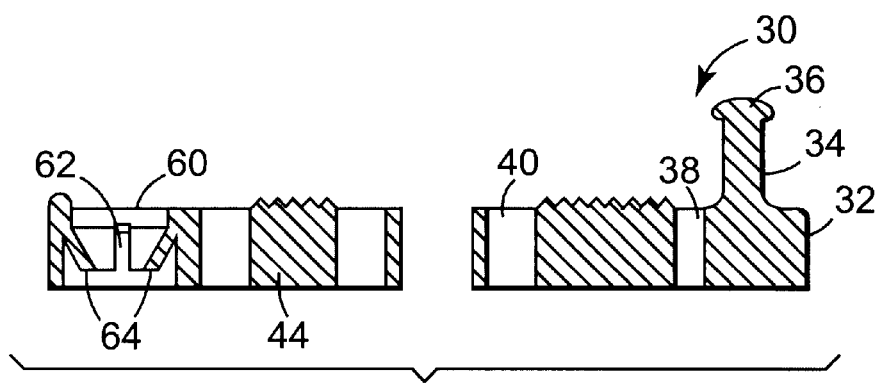
FIG. 6 is a cross-sectional view of an exemplary embodiment of the reinforcing fastener guide of the present invention generally corresponding to that of FIG. 2.

Turning now to FIG. 2, an exemplary embodiment of the present invention illustrating the features thereof is represented as a novel reinforcing fastener guide generally indicated by reference numeral 30. In accordance with the teachings of the present invention, this exemplary embodiment of reinforcing fastener guide 30 is fixedly mountable upon at least one surface of a medical device (not shown) as follows: reinforcing fastener guide 30 can be constructed or manufactured in a configuration as simple as a single, generally circular body 32 provided with at least one locking pin 34 projecting therefrom. Preferably, as illustrated in FIG. 2, a plurality of locking pins 34 are utilized as this combination distributes loads over a larger area of the medical implant. As shown in FIG. 2, each of locking pins 34 is provided with an enlarged head 36 at its projecting tip. For additional understanding of this construction, FIG. 6 provides a cross-sectional view illustrating these details.

It should be emphasized that body 32 need not be formed as the generally circular structure of FIG. 2 in order to come within the scope and teachings of the present invention. Rather, it is contemplated as being within the scope of the present invention to form body 32 in a wide variety of geometric shapes ranging from simple bars and crescents through polygons, circles, and the like. When formed into the generally circular shape shown, reinforcing fastener guide 30 defines or provides a central location for at least one or for a plurality of fastener apertures including central fastening aperture 38 and additional fastening apertures 40. It should be noted that only the fundamental features of body 32 are illustrated in FIGS. 2 and 6. Those skilled in the art will appreciate that additional surface features, shapes, and details may be provided as desired, including projecting knobs, hooks, curbs, tabs, buttons, loops or the like.

Additionally, body 32 can be formed of any available surgically compatible material having sufficient compressive and tensile strength to function in its intended environment as a reinforcing fastener guide distributing loads into an implantable medical device. Exemplary materials include surgical grade metals such as stainless steel and titanium as well as surgical grade plastics and composites which can include virtually any known or contemplated biologically compatible polymers. It is also contemplated that a bioresorbable material could be used. In the exemplary embodiment of reinforcing fastener guide 30 shown, body 32 is formed of acetal. However, it should be emphasized that this is not a limiting feature of the present invention and that alternative materials may be utilized as appropriate.

In its simplest form, reinforcing fastener guide 30 is fixedly mounted upon a medical device through engagement of locking pins 34 into interlocking engagement with a surface of the medical device (not shown). Once in-place, the enlarged heads 36 of each of locking pins 34 retains body 32 fixed firmly in position upon the surface of the medical implant. Thus, any stresses or loads transmitted into reinforcing fastener guide 32 during surgical implantation or after, will be distributed into a much larger area of the compression ring 33 (e.g. see FIG. 5) of the medical implant by body 32 and, eventually, locking pins 34. In this manner, focused, potentially damaging stresses are dispersed into a greater portion of the medical implant, reducing their impact and the potential for subsequent wear and distortion.

Figure 7:
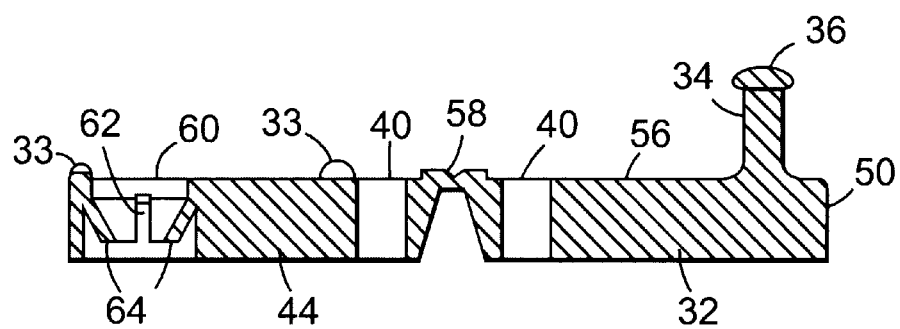
FIG. 7 is a cross sectional view of an exemplary embodiment of the reinforcing fastener guide of the present invention generally corresponding to that of FIG. 4.
Figure 7A:
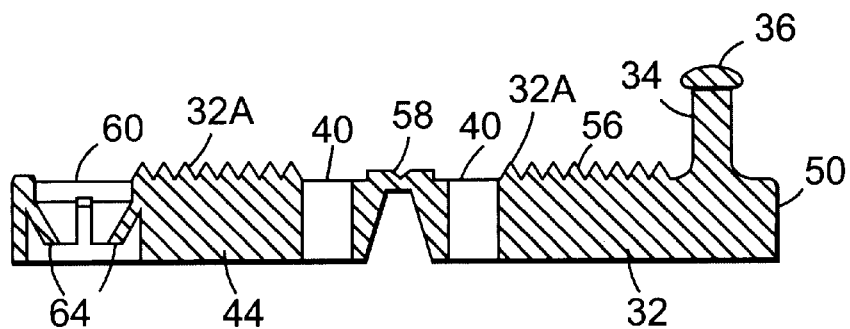
FIG. 7A is a cross sectional view of an alternative embodiment of mating surfaces of the fastener guide shown in FIG. 7.
Figure 7B:
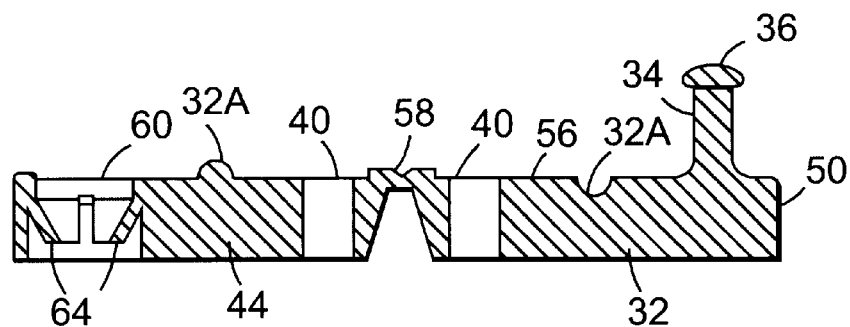
FIG. 7B is a cross sectional view of an alternative embodiment of mating surfaces of the fastener guide shown in FIG. 7.
Figure 7C:
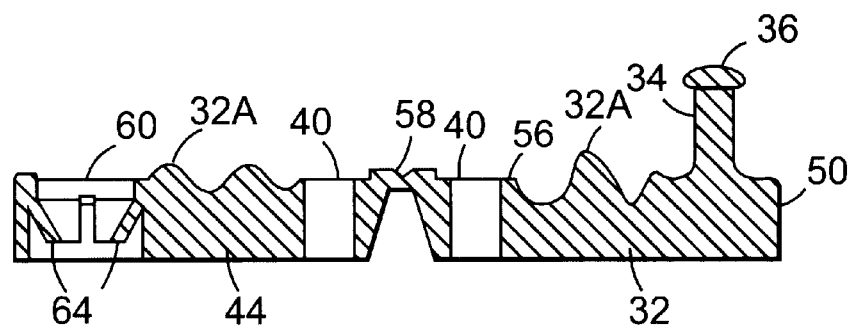
FIG. 7C is a cross sectional view of an alternative embodiment of mating surfaces of the fastener guide shown in FIG. 7.

In another embodiment as disclosed in FIGS. 7A, 7B and 7C, the reinforcing fastener guide 30 is constructed such that the mating surfaces of body 32 and the backing plate 44 have opposing formations 32A that mate and engage one another when the body 32 and plate 44 are brought together. The formations can take on numerous shapes such as a saw-tooth configuration (FIG. 7A), a dimpled pattern (FIG. 7B) and a rounded wave configuration (FIG. 7C). These mating formations 32A serve to enhance the ability of the fastener guide 30 to attach to the support 16 by providing more surface area with the ability to grasp and hold the support 16 material. The mating formations can also take on a waffle-like pattern or similar textured surface pattern.

Figure 5:
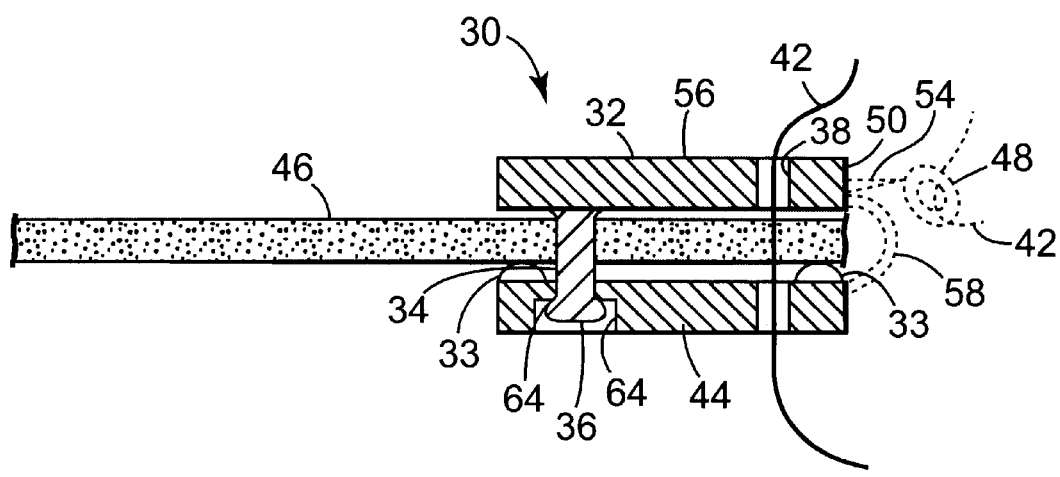
FIG. 5 is a cross sectional view of an exemplary medical implant of the present invention illustrating additional functional aspects thereof.

As further illustrated in FIG. 2 and FIG. 6, at least one central fastening aperture 38 is provided in body 32 of reinforcing fastener guide 30. As desired or necessary for the intended function of the implant, a plurality of central fastening apertures 38 or even additional fastening apertures 40 can be provided in body 32. Regardless of the number, these fastening apertures are intended to receive at least one surgical fastener, itself intended to fixate the implant in position within the patient. As illustrated in FIG. 5, an exemplary surgical fastener within the scope of the present invention is represented by sutures 42. However, alternative surgical fasteners including rivets, pins, screws, studs, and the like are contemplated as being (within scope of the present invention and may be utilized in place of sutures 42. Either way, those skilled in the art will appreciate that it is possible to distribute potentially damaging tensile loads through a larger area of the implant by utilizing larger numbers of surgical fasteners or sutures in conjunction with the reinforcing fastener guides of the present invention.

Returning to FIG. 2, an additional alternative aspect of the present invention is illustrated in conjunction with body 32. More specifically, this exemplary reinforcing fastener guide 30 may also include a complementary reinforcing fastener guide backing plate 44 dimensioned to receive locking pins 34 in a fixed, interlocking relationship. This interlocking relationship is further illustrated in FIG. 6 in conjunction with a generally planar portion of a medical device. As shown in FIG. 2, backing plate 44 is provided with fastening apertures 38 and 40 which correspond in position to those provided in body 32.

Thus, as illustrated in FIG. 5, when body 32 and backing plate 34 are fixed in interlocking relationship sandwiching a generally planar portion of a medical device 46 therebetween, they function to securely retain reinforcing fastener guide 30 in discrete engagement with medical device 46 so that any loads transmitted into reinforcing fastener guide 30 are distribute by locking pins 34 completely throughout the extent of medical device 46 sandwiched between body 30 and backing plate 44. As a result, potential damaging loads are evenly dispersed and attenuated through medical device 46 while locking pins 34 are retained within backing plate 44 so that they resist pulling through or distorting medical device 46 as they function to transmit these loads.

Figure 3:
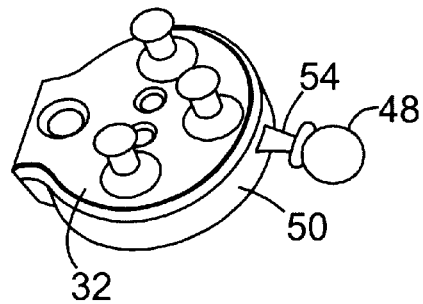
FIG. 3 is a perspective view of and alternative embodiment of the reinforcing fastener guide of the present invention provided with an external ring.

Referring now to FIG. 3, another alternative embodiment of the present invention is illustrated wherein the reinforcing fastener guide 30 is provided with an external ring 48 projecting from the peripheral edge 50 of body 32. A cross-sectional illustration of this alternative embodiment of the present invention is provided in FIG. 8.

Figure 8:
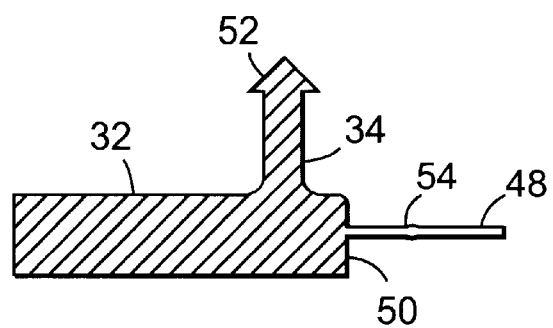
FIG. 8 is a cross sectional view of an exemplary embodiment of the reinforcing fastener guide of the present invention generally corresponding to that of FIG. 3.

However, it should be noted that the reinforcing fastener guide 30 of FIG. 8 is provided with a generally, conical enlarged head 52, as opposed to the more spherical enlarged head 36 of FIG. 2 and FIG. 6. Those skilled in the art will appreciate that the sharper point provided by this alternative, conical enlarged head 52 enables the projecting locking pin 34 to pierce membranes or weaves on its own, rather than through a previously provided passageway in the surface of the medical device enhanced by the present invention.

Further illustrated in FIG. 3 and FIG. 8 is a pivot 54 disposed between external ring 48 and peripheral edge 50 of body 32. Pivot 54 provides added degree of available adjustment to external ring 48 and enables the implanting surgeon to rotate or reposition external ring 48 as necessary or desired to facilitate the passing of suture 42 through external ring 48 as part of the medical device implantation attachment process.

External ring 48 with or without pivot 54 can be positioned in alternative locations on body 32 or backing plate 44 as desired. Exemplary alternative locations include opposing sides of peripheral edge 50 as well as external body surface 56 of body 32 and corresponding structural features on backing plate 44. As will be appreciated by those skilled art, the present invention provides the medical implant manufacturer or the reinforcing fastener guide manufacturer, and the implanting surgeon with a wide range of variations regarding the number of fastening apertures and external rings that may be incorporated into individual reinforcing fastener guides. It is contemplated as being within the scope of the present invention to manufacturer external ring 48 out of surgical grade metal alloys such as stainless steel or titanium. However, alternative materials having appropriate wear resistance and tensile strength are also within scope of the present invention for this purpose.

Figure 4:
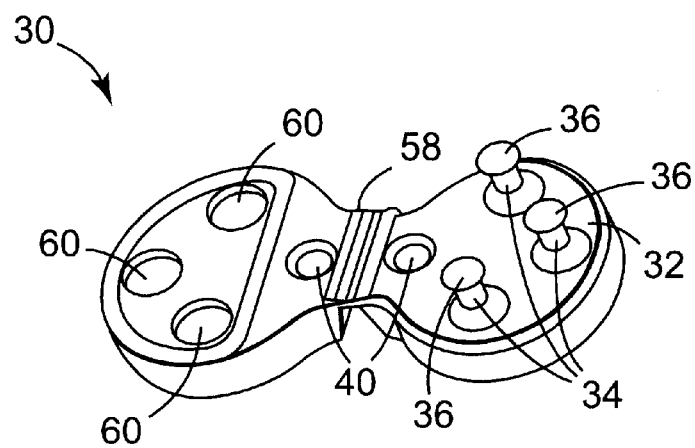

Turning next to FIG. 4, an additional alternative embodiment of reinforcing fastener guide 30 of the present invention is illustrated wherein body 32, provided with a plurality of projecting locking pins 34 and a single fastening aperture 40, as well as corresponding structures on backing plate 44, is connected to backing plate 44 by hinge 58. As further illustrated in FIG. 7, hinge 58 makes it possible for the combined body 32 and backing plate 44 reinforcing fastener guide to be effectively "snapped" over an edge of a generally planar portion of a medical device 46 with a single motion.

Thus, this alternative embodiment of the present action is particularly well suited for simplified fixed attachment to a medical implant such as a urethral sling immediately prior to or during an implantation procedure. Further, it should be noted that providing such a hinge reinforcing fastener guide with conical enlarged heads 52 on projecting locking pins 34 further simplifies this hinged attachment process by enabling the device to self-pierce through the planar portion of the medical device as the reinforcing fastener guide 30 is snapped about the edge thereof.

Turning next to the cross-sectional illustrations of FIGS. 6 and 7, the details of an exemplary fixation interlock 60 in accordance with the teachings of the present invention are provided. In this exemplary embodiment, fixation interlock 60 generally comprises an enlarged receiving bore 62 provided in backing plate 44 and complimentarily dimensioned to receive and retain in fixed interlocking relationship enlarged head 36 and projecting shaft of locking pin 34 projecting from body 32.

This exemplary fixation interlock feature is further enabled by the teachings of the present invention through the provision of at least one enlarged receiving bore 62 with at least one deflectable flange 64 which will distort and facilitate the passage of enlarged head 36 through enlarged receiving bore 62 and then snap back into a retracted, smaller diameter, normal position underneath enlarged head 36 as locking pin 34 is fully engaged within enlarged receiving bore 62 and backing plate 44. Thus, in a single compressive motion, an implanting surgeon or device manufacturer can permanently interlock body 32 arid backing plate 44 of reinforcing fastener guide 30 together into position retaining the planar portion of a medical implant therebetween fixated by the fixedly interlocked locking pins 34.

Once again, it should be appreciated that this exemplary fixation interlock mechanism is provided for purposes of illustration only and is not, itself, a limiting feature of the present invention. Rather, alternative interlocks as known in the art are contemplated as being within the scope of the present invention.

Consistent with the teachings of the present invention, these elements, features, and advantages can be applied to virtually any existing medical device. For example, the present invention can be utilized to enhance the functional longevity and to facilitate the implantation of a urethral sling. Such an improved medical device, in accordance with the teachings of the present invention, would comprise a generally planar sling provided with a plurality of reinforcing fastener guides 30, each of the which is disposed adjacent to the edges of the sling and fixedly attached thereto. The exact positioning of each reinforcing fastener guide 30 can be based upon previous experience with the implantation and support of such implantable medical devices. For example, a urethral sling having a support could be provided with a reinforcing fastener guide 30 fixedly attached at each opposing corner of the support. This would enable the implanting surgeon to suture or fasten these opposing corners to the pelvic structure, e.g., the pelvic ischia, much like a conventional implantation process, only with much greater ease.

Utilization of the reinforcing fastener guide 30 provided by the present invention greatly facilitates the surgical implantation of medical devices so equipped by eliminating steps normally present in a conventional implantation process as well as simplifying the remaining suturing or fastening steps. Thus, in accordance with the teachings of the present invention, an implantation method for enhancing the functional longevity and for facilitating the implantation of implantable medical devices is provided which comprises the following steps.

First, at least one reinforcing fastener guide is fixedly mounted on at least a portion of the medical device prior to or during the implantation process. Next, the medical device so equipped is positioned within a patient's body at a desired implantation site. Finally, at least one surgical fastener is placed through each of the at least one reinforcing fastener guides. For example, an exemplary surgical fastener suitable for practicing the method of the present invention is a conventional suture.

Thus, as a result of the present invention's teachings, through utilization of the reinforcing fastener guides 30, the implanting surgeon is provided with a plurality of readily identifiable, pre-positioned surgical fastener locations for fixating the implantable medical device in position. Because of the unique structure of reinforcing fastener guides 30, these locations can be located easily through touch or sight during the implantation process. This eliminates the possibility of missing a suitable fixation location and eliminates the need for the implanting surgeon to either locate hard to find pre-existing holes in the medical implant or to create such holes as part of the process. As a result, the present invention substantially eliminates the risk of potential damage to the medical device occurring as part of the implantation process. Further, the apparatus of the present invention substantially eliminates the potential for distortion of the implant over its useful life, thus increasing its functional longevity.

The present invention is also reasonably easy to manufacture. In one embodiment, the fastener guide 30 can be injection molded. Indeed, in one embodiment, it is contemplated that the guide could be injected onto the support 16 itself, thereby enhancing the advantages of the guide 30.

Other embodiments, features, and advantages of the present invention will be apparent to those skilled in the art from a consideration of the foregoing specification as well as through practice of the invention and alternative embodiments and methods disclosed herein. Therefore, it should be emphasized that the specification and examples are exemplary only, and that the true scope and spirit of the invention is limited only by the following claims.

What is claimed is:

1. A self-affixing apparatus for enhancing the functional longevity and for facilitating the implantation of medical devices having first and second major surfaces, said apparatus comprising:

a reinforcing fastener guide having surfaces for abutting the first and second major surfaces of the medical device to fixedly mount on the medical device, wherein said reinforcing fastener guide is a generally circular, planar disc having at least one fastener aperture therethrough, and wherein said medical device is a urethal sling provided with a plurality of said reinforcing fastener guides.

2. The apparatus of claim 1, wherein said reinforcing fastener guide is made from a material selected from the group consisting of surgical grade metals and polymers.

3. The apparatus of claim 2, wherein said reinforcing fastener guide is made from surgical-grade stainless steel.

4. An apparatus for enhancing the functional longevity and for facilitating the implantation of medical devices, said apparatus comprising:
   a reinforcing fastener guide fixedly mountable upon at least one surface of a medical device, and
   at least one external ring affixed to said reinforcing fastener guide.

5. The apparatus of claim 4, wherein said external ring is pivotally attached to said reinforcing fastener guide.

6. The apparatus of claim 4, wherein said external ring is made from surgical grade stainless steel.

7. A self-affixing apparatus for enhancing the functional longevity and for facilitating the implantation of medical devices having first and second major surfaces, said apparatus comprising:
   a reinforcing fastener guide having surfaces for abutting the first and second major surfaces of the medical device to fixedly mount on the medical device,
   wherein said reinforcing fastener guide includes a generally circular, planar disc having at least one fastener aperture therethrough, and
   where the circular, planar disc has grasping formations.

8. A self-affixing apparatus for enhancing the functional longevity and for facilitating the implantation of medical devices having first and second major surfaces, said apparatus comprising:
   a reinforcing fastener guide having surfaces for abutting the first and second major surfaces of the medical device to fixedly mount on the medical device,
   wherein said reinforcing fastener guide is provided with at least one fixation interlock, and
   wherein the fixation interlock comprises a locking pin and the locking pin pierces/cores through the medical device prior to locking engagement.

9. A self-affixing apparatus for enhancing the functional longevity and for facilitating the implantation of medical devices having first and second major surfaces, said apparatus comprising:
   a reinforcing fastener guide having surfaces for abutting the first and second major surfaces of the medical device to fixedly mount on the medical device,
   wherein said reinforcing fastener guide is provided with at least one fixation interlock, and
   wherein said fixation interlock comprises:
      at least one locking pin projecting from said reinforcing fastener guide into locking engagement with said medical device.

10. The apparatus of claim 9, wherein said fixation interlock further comprises:
   a complimentary reinforcing fastener guide backing plate dimensioned to receive said at least one locking pin in fixed, interlocking relationship.

11. The apparatus of claim 10, wherein backing plate is hinged to said reinforcing fastener guide.

12. The apparatus of claim 10, wherein said reinforcing fastener guide and said backing plate include mating grasping formations.

13. The apparatus of claim 9, wherein said at least one locking pin is configured to pierce and retain a generally planar portion of a medical device.

14. The apparatus of claim 13, wherein said medical device is a sling.

15. A self-affixing apparatus for enhancing the functional longevity and for facilitating the implantation of medical devices having first and second major surfaces, said apparatus comprising:
   a reinforcing fastener guide fixedly mountable upon the first and second major surfaces of a medical device,
   wherein said reinforcing fastener guide is provided with at least one fixation interlock, and
   further comprising a compression ring,
   the fixation interlock comprises at least one locking pin projecting from said reinforcing fastener guide and the locking pin pierces/cores through the medical device prior to locking engagement,
   wherein the compression ring compresses the medical device upon pin locking and thus distributes stresses along a larger surface area away from the pierced/cored holes.

16. An implantation method for enhancing the functional longevity while facilitating the implantation of a medical device, said method comprising the steps of:
   fixedly mounting at least one reinforcing fastener guide to at least one portion of a medical device prior to implantation of said device;
   positioning said reinforced fastener guide mounted medical device at a desired location within a patient's body; and
   placing at least one surgical fastener through each of said at least one reinforcing fastener guide.

17. The method of claim 16, wherein said surgical fastener is a suture.

18. The method of claim 16, wherein said medical device is a urethral sling.

19. A generally planar urethral sling provided with a plurality of self-affixing apparatuses for enhancing the functional longevity and for facilitating the implantation of the urethral sling, the urethral sling having first and second major surfaces and edges, said self-affixing apparatuses comprising:
   a reinforcing fastener guide fixedly mountable upon the first and second major surfaces of the urethral sling,
   wherein said reinforcing fastener guide is provided with at least one fixation interlock, and
   the self-affixing apparatuses being disposed adjacent the edges of said urethral sling and fixedly interlocked thereto.

* * * * *